United States Patent
Jung et al.

(10) Patent No.: US 11,416,950 B2
(45) Date of Patent: Aug. 16, 2022

(54) CUSTOMIZED COSMETIC MANUFACTURING APPARATUS AND METHOD THEREOF

(71) Applicant: TOUN28 Inc., Gyeonggi-do (KR)

(72) Inventors: Yangsuk Jung, Gyeonggi-do (KR);
Jihoon Ahn, Gyeonggi-do (KR);
Bumhee Chung, Gyeonggi-do (KR)

(73) Assignee: TOUN28 Inc.

( * ) Notice: Subject to any disclaimer, the term of this patent is extended or adjusted under 35 U.S.C. 154(b) by 830 days.

(21) Appl. No.: 16/328,127

(22) PCT Filed: Aug. 28, 2017

(86) PCT No.: PCT/KR2017/009361
§ 371 (c)(1),
(2) Date: Feb. 25, 2019

(87) PCT Pub. No.: WO2018/044010
PCT Pub. Date: Mar. 8, 2018

(65) Prior Publication Data
US 2019/0188809 A1  Jun. 20, 2019

(30) Foreign Application Priority Data

Aug. 31, 2016 (KR) .......... 10-2016-0111449
May 30, 2017 (KR) .......... 10-2017-0067138

(51) Int. Cl.
*A61B 5/00* (2006.01)
*G06Q 50/04* (2012.01)
(Continued)

(52) U.S. Cl.
CPC .......... *G06Q 50/04* (2013.01); *A61B 5/00* (2013.01); *A61B 5/01* (2013.01); *G06Q 50/10* (2013.01);
(Continued)

(58) Field of Classification Search
CPC .......... G06Q 50/04; G06Q 50/10; A61B 5/00; A61B 5/01; A61B 5/442; A61B 5/443; B01F 33/8442; Y02P 90/30
(Continued)

(56) References Cited

U.S. PATENT DOCUMENTS 9,522,112 B2 * 12/2016 Dubois ............... A61Q 19/005
2009/0076639 A1 * 3/2009 Pak ..................... G06Q 10/08
700/106
(Continued)

FOREIGN PATENT DOCUMENTS

CN 103717109 A 4/2014
CN 104769632 A 7/2015
(Continued)

OTHER PUBLICATIONS

International Search Report dated Dec. 5, 2017.
Chinese Search Report dated Dec. 27, 2020 pertaining to CN Application No. 201710451457.8 filed Jun. 15, 2017.

*Primary Examiner* — May A Abouelela
(74) *Attorney, Agent, or Firm* — Dinsmore & Shohl LLP (57) ABSTRACT

An apparatus for manufacturing customized cosmetics according to an exemplary embodiment of the present invention may manufacture customized cosmetics in consideration of an individual skin characteristic and external environment information by combining a dosage form reference component corresponding to a skin state measured by subdividing a face of a user according to each predetermined region and an auxiliary dosage form reference component corresponding to the external environment information.

8 Claims, 6 Drawing Sheets

(51) Int. Cl.
*A61B 5/01* (2006.01)
*G06Q 50/10* (2012.01)
*B01F 33/84* (2022.01)

(52) U.S. Cl.
CPC ........... *A61B 5/442* (2013.01); *B01F 33/8442* (2022.01); *Y02P 90/30* (2015.11)

(58) Field of Classification Search
USPC ....................................................... 600/306
See application file for complete search history.

(56) References Cited

U.S. PATENT DOCUMENTS

| | | | | |
|---|---|---|---|---|
| 2009/0220415 | A1* | 9/2009 | Shachaf | A61B 5/444 424/9.8 |
| 2010/0030058 | A1* | 2/2010 | Mammone | A61B 5/442 600/407 |
| 2010/0185064 | A1* | 7/2010 | Bandic | A61B 5/444 600/306 |
| 2011/0301441 | A1* | 12/2011 | Bandic | A61B 5/0537 600/306 |
| 2012/0172685 | A1* | 7/2012 | Gilbert | A61B 5/0077 600/306 |
| 2014/0081095 | A1* | 3/2014 | Krishnan | A61B 5/443 600/306 |
| 2016/0100790 | A1* | 4/2016 | Cantu | A61B 5/445 600/437 |
| 2016/0135730 | A1* | 5/2016 | Arai | A61B 5/0077 600/476 |
| 2016/0154992 | A1* | 6/2016 | Shinoda | G06V 40/161 382/103 |
| 2017/0056685 | A1* | 3/2017 | Harvey | A61B 5/443 |
| 2017/0127998 | A1* | 5/2017 | Jang | A61B 5/1079 |
| 2018/0014777 | A1* | 1/2018 | Amir | A61B 5/444 |
| 2018/0033174 | A1* | 2/2018 | Kimura | G16H 30/40 |
| 2018/0352937 | A1* | 12/2018 | Vandier | A61B 5/6803 |

FOREIGN PATENT DOCUMENTS

| | | |
|---|---|---|
| KR | 10-2006-0109797 A | 10/2006 |
| KR | 10-2007-0006288 A | 1/2007 |
| KR | 10-2009-0124140 A | 12/2009 |
| KR | 10-2013-0062845 A | 6/2013 |
| KR | 10-2014-0072685 A | 6/2014 |
| KR | 10-2016-0008119 A | 1/2016 |
| KR | 10-2016-0095792 A | 8/2016 |
| WO | 2013-021595 A1 | 2/2013 |

* cited by examiner

T zone (102)

| Dosage form / Measurement value | Moisture | Wrinkle | Elasticity | Sebum care |
|---|---|---|---|---|
| Moisture | 3 | | | |
| Wrinkle | | 4 | | |
| Elasticity | | | 6 | |
| Sebum care | | | | 7 |

U zone

| Dosage form / Measurement value | Moisture | Wrinkle | Elasticity | Sebum care |
|---|---|---|---|---|
| Moisture | 7 | | | |
| Wrinkle | | 3 | | |
| Elasticity | | | 4 | |
| Sebum care | | | | 6 |

O zone (104)

| Dosage form / Measurement value | Moisture | Wrinkle | Elasticity | Sebum care |
|---|---|---|---|---|
| Moisture | 6 | | | |
| Wrinkle | | 8 | | |
| Elasticity | | | 3 | |
| Sebum care | | | | 4 |

N zone

| Dosage form / Measurement value | Moisture | Wrinkle | Elasticity | Sebum care |
|---|---|---|---|---|
| Moisture | 4 | | | |
| Wrinkle | | 6 | | |
| Elasticity | | | 5 | |
| Sebum care | | | | 3 |

FIG. 4

| Dosage form | Measurement value | Environment information | | | | Hormone cycle | | |
|---|---|---|---|---|---|---|---|---|
| | Based on four regions | Fine dust | Temperature | Humidity | Ultraviolet rays | Estrogen active phase | Menstruating | Progesterone active phase |
| Moisture | 1~8 | N/A | 1~5 | 1~5 | 1~5 | N/A | Yes | Yes |
| Wrinkle | 1~8 | N/A | N/A | 1~5 | N/A | N/A | N/A | N/A |
| Elasticity | 1~8 | N/A | N/A | 1~5 | N/A | N/A | N/A | N/A |
| Sebum care | 1~8 | 1~5 | N/A | N/A | N/A | N/A | N/A | Limited |

Fine dust measurement value

| Reference value (µm) | Measurement point |
|---|---|
| over 201 | 5 |
| 121~200 | 4 |
| 81~120 | 3 |
| 31~80 | 2 |
| 0~30 | 1 |

Temperature measurement value

| Reference value | Measurement point |
|---|---|
| over 31 | 5 |
| 28~31 | 4 |
| 25~28 | 3 |
| 21~25 | 2 |
| under 21 | 1 |

Humidity measurement value

| Reference value (%) | Measurement point |
|---|---|
| 0~20 | 5 |
| 20~40 | 4 |
| 40~60 | 3 |
| 60~80 | 2 |
| 80~100 | 1 |

Ultraviolet ray measurement value

| Reference value | Measurement point |
|---|---|
| 9.0~ | 5 |
| 7.0~8.9 | 4 |
| 5.0~6.9 | 3 |
| 3.0~4.9 | 2 |
| 0.0~2.9 | 1 |

| Classification | | Month | 1 | 2 | 3 | 4 | 5 | 6 | 7 | 8 | 9 | 10 | 11 | 12 |
|---|---|---|---|---|---|---|---|---|---|---|---|---|---|---|
| Weather change measurement value | Environment information | Fine dust (μm) | 49 | 84 | 71 | 45 | 45 | 35 | 30 | 34 | 29 | 45 | 33 | 48 |
| | | Temperature(°C) | -2 | 0 | 6 | 13 | 18 | 22 | 25 | 26 | 21 | 15 | 7 | 0 |
| | | Humidity(%) | 59 | 58 | 58 | 56 | 63 | 68 | 79 | 76 | 69 | 64 | 62 | 60 |
| | | Ultraviolet rays | 1.6 | 1.7 | 4.3 | 5.8 | 6.5 | 6.9 | 7.9 | 8.2 | 6.3 | 4 | 2.1 | 1.7 |
| Weather change correction value | First correction value (80%) | Moisture | 8% | 7% | 6% | 4% | 4% | 2% | N/A | N/A | 2% | 4% | 6% | 7% |
| | | Sebum (oily)01~05 | N/A | N/A | 2% | 3% | 4% | 6% | 8% | 6% | 3% | 3% | 2% | N/A |
| | | Sebum (dry)06~010 | 11% | 10% | 9% | 7% | 5% | 2% | N/A | N/A | 2% | 5% | 8% | 10% |
| | | Whitening | N/A | N/A | N/A | 1% | 3% | 5% | 8% | 5% | 3% | 2% | N/A | N/A |
| | | Wrinkle | 8% | 6% | 4% | 3% | 2% | 1% | N/A | N/A | 3% | 4% | 6% | 8% |
| | Second correction value (20%) | Anti-contamination | 4% | 8% | 10% | 10% | 8% | 6% | 4% | 2% | 2% | 6% | 4% | 4% |
| | | UV component | 4% | 4% | 8% | 8% | 12% | 14% | 12% | 14% | 10% | 8% | 6% | 4% |
| | | Hydro Controler | 12% | 8% | 2% | 2% | 0% | 0% | 4% | 4% | 8% | 6% | 10% | 12% |

CUSTOMIZED COSMETIC MANUFACTURING APPARATUS AND METHOD THEREOF

CROSS-REFERENCE TO RELATED APPLICATIONS

This application is the U.S. national stage of PCT/KR2017/009361 filed Aug. 28, 2017, which claims priority of Korean Patent Application No. 10-2016-0111449 filed on Aug. 31, 2016 and Korean Patent Application No. 10-2017-0067138 filed on May 30, 2017 which are incorporated herein by reference in their entirety.

FIELD OF THE INVENTION

An apparatus and a method for manufacturing customized cosmetics are provided.

BACKGROUND OF THE INVENTION

Cosmetics are used for maintaining or managing skin health of an individual. For example, the cosmetics may maintain skin moisture. Cosmetics to which a functional component is added are increasingly used. Further, the cosmetics are divided and produced according to the type of skin of a user. The skin of a user may be divided into oily skin, normal skin, dry skin, and the like, and cosmetics suitable for the divided skin types have been produced. Recently, damage to skin due to environmental contamination, such as depletion of the ozone layer and air pollution, and stress, have gradually increased, and it is necessary for a user to select and use cosmetics that are suitable for the type of skin of the user.

However, skin problems may be generated due to a specific component contained in cosmetics according to a body change or an external environment change of a user. However, since cosmetics are generally mass produced by a manufacturing company, it may be difficult for users to receive appropriate cosmetics, of which the type of users' skin or information about an external environment change is reflected, at an appropriate time.

The present disclosure has been made in an effort to provide an apparatus and a method of manufacturing customized cosmetics, which are capable of manufacturing customized cosmetics in consideration of an individual skin characteristic and external environment information by combining a dosage form reference component corresponding to a skin state measured by subdividing a face of a user according to each predetermined region, and an auxiliary dosage form reference component corresponding to external environment information.

SUMMARY OF THE INVENTION

An exemplary embodiment of the present disclosure provides an apparatus for manufacturing customized cosmetics, the apparatus including: a memory unit, which stores a dosage form reference component skin measurement value divided based on each face region of a user, an auxiliary dosage form reference component measurement value separately divided from the dosage form reference component skin measurement value, a dosage form reference component skin reference value corresponding to the dosage form reference component skin measurement value, and an auxiliary dosage form reference component reference value corresponding to the auxiliary dosage form reference component measurement value; and a control unit, which is operated by a processor of an information processing device, and compares the dosage form reference component skin measurement value with the dosage form reference component skin reference value and calculates a dosage form reference component skin measurement point, compares the auxiliary dosage form reference component measurement value with the auxiliary dosage form reference component reference value and calculates an auxiliary dosage form reference component measurement point, determines a dosage form reference component based on the dosage form reference component skin measurement point, determines an auxiliary dosage form reference component based on the auxiliary dosage form reference component measurement point, and determines a final dosage form component by combining the dosage form reference component and the auxiliary dosage form reference component.

Another exemplary embodiment of the present disclosure provides a method of manufacturing customized cosmetics, the method including: storing a dosage form reference component skin measurement value divided based on each face region of a user, and an auxiliary dosage form reference component measurement value separately divided from the dosage form reference component skin measurement value; and after the dosage form reference component skin measurement value and the auxiliary dosage form reference component measurement value are stored, reading a dosage form reference component skin reference value corresponding to the dosage form reference component skin measurement value and an auxiliary dosage form reference component reference value corresponding to the auxiliary dosage form reference component measurement value from a memory unit, and comparing the dosage form reference component skin measurement value with the dosage form reference component skin reference value and calculating a dosage form reference component skin measurement point, comparing the auxiliary dosage form reference component measurement value with the auxiliary dosage form reference component reference value and calculating an auxiliary dosage form reference component measurement point, determining a dosage form reference component based on the dosage form reference component skin measurement point, determining an auxiliary dosage form reference component based on the auxiliary dosage form reference component measurement point, and determining a final dosage form component by combining the dosage form reference component and the auxiliary dosage form reference component.

The face region of the user may include a first region, which is an external region, and a second region, which is an internal region, the first region may include a T zone covering a forehead line and a nose line, which are upper portions in the external region of the face region, and a U zone covering both lateral lines and a chin line, which are lower portions in the external region of the face region, and the second region may include an O zone covering both eye surrounding lines and cheek lines in the internal region of the face region, and an N zone covering a nose surrounding line and a mouth surrounding line in the internal region of the face region.

The dosage form reference component skin measurement value may include a moisture component skin measurement value, a wrinkle component skin measurement value, an elasticity component skin measurement value, and a sebum care component skin measurement value, and the auxiliary dosage form reference component measurement value may include one or more of a weather change measurement value including a fine dust measurement value, a temperature measurement value, a humidity measurement value, and an ultraviolet ray measurement value, and a menstrual cycle measurement value.

The dosage form reference component skin measurement value may include a moisture component skin measurement value, a wrinkle component skin measurement value, a whitening component skin measurement value, and a sebum care component skin measurement value, and the auxiliary dosage form reference component measurement value may include one or more of a weather change measurement value including a fine dust measurement value, a temperature measurement value, a humidity measurement value, and an ultraviolet ray measurement value, and a menstrual cycle measurement value.

The method may further include receiving an input of a selection signal for the kind of customized cosmetics, in which the kind of customized cosmetics may include a premium type and a standard type, the face region of the user may include a first region, which is an external region, and a second region, which is an internal region, when the customized cosmetics of the premium type are manufactured, a dosage form reference component-specific skin measurement point may be calculated by a predetermined reference among the plurality of dosage form reference component skin measurement points calculated in the first region and the second region based on each dosage form reference component, two high rank points including the first rank skin measurement point and the second rank skin measurement point may be selected among the dosage form reference component-specific skin measurement points, and the final dosage form component may be set based on the first rank skin measurement point and the second rank skin measurement point, and when the customized cosmetics of the standard type are manufactured, a dosage form reference component-specific skin measurement point may be calculated by a predetermined reference among the plurality of dosage form reference component skin measurement points calculated in the first region, two high rank points including the first rank skin measurement point and the second rank skin measurement point may be selected among the dosage form reference component-specific skin measurement points, and the final dosage form component may be set based on the first rank skin measurement point and the second rank skin measurement point.

The face region of the user may include a first region, which is an external region, and a second region, which is an internal region, and two high rank points including the first rank skin measurement point and the second rank skin measurement point may be selected among the plurality of dosage form reference component skin measurement points calculated in the first region and the second region based on each dosage form reference component, and the final dosage form component may be set based on the final first rank skin measurement point and the second rank skin measurement point calculated by adding a predetermined weather change correction value to each of the first rank skin measurement point and the second rank skin measurement point.

The weather change correction value may be set according to a time period-specific weather change measurement value, and the weather change correction value may include a first correction value including a moisture component correction value, a sebum component correction value, a whitening component correction value, and a wrinkle component correction value, and a second correction value including an anti-contamination component correction value, an ultraviolet component correction value, and a hydro controller component correction value.

According to the exemplary embodiment of the present disclosure, it is possible to manufacture customized cosmetics appropriate for a skin type of a user and an external environment state based on a dosage form reference component skin measurement value measured by dividing a face region of the user into subregions, and provide the manufactured customized cosmetics at an appropriate time.

Further, according to the exemplary embodiment of the present disclosure, it is possible to provide a user with various information, based on which the user is capable of selecting appropriate cosmetics, thereby providing a guide function for a lifestyle and skin management of the user.

Further, according to the exemplary embodiment of the present disclosure, it is possible to enable a user to particularly check the kind of skin problems and a region including the skin problems in a user's face region through skin measurement, in which the user's face region is sub-divided into a first region and a second region, when skin of the user is measured.

Further, a user may regularly measure the skin of his/her face region, so that the user may more precisely check a skin state of the face region responding to his/her body change or an external environment change, thereby obtaining reliability in the skin measurement.

DETAILED DESCRIPTION OF THE PREFERRED EMBODIMENTS

Technical terms used herein are simply provided for mentioning a specific exemplary embodiment, and are not intended to limit the present disclosure. Singular forms used herein include plural forms unless they have definitely opposite meanings. The meaning of "including" used in the specification gives shape to specific characteristics, regions, integers, steps, operations, elements, and/or components, and does not exclude the existence or addition of other specific characteristics, regions, integers, steps, operations, elements, components, and/or groups.

All the terminologies including technical terms and scientific terms used herein have the same meanings that those skilled in the art generally understand. Terms defined in dictionaries are construed to have meanings corresponding to related technical documents and the present description, and they are not construed as idealized or very official meanings, if not so defined.

The present disclosure will be described more fully hereinafter with reference to the accompanying drawings, in which exemplary embodiments of the disclosure are shown. As those skilled in the art would realize, the described embodiments may be modified in various different ways, all without departing from the spirit or scope of the present disclosure.

Figure 1:
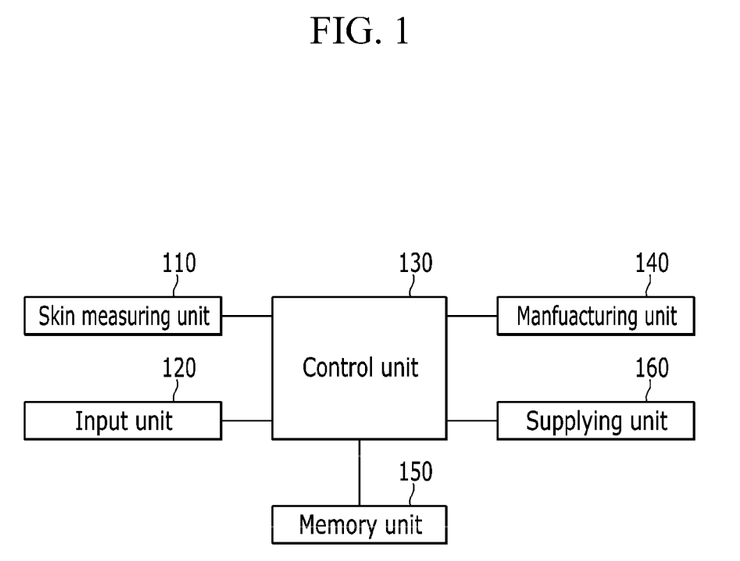
FIG. 1 is a diagram schematically illustrating an apparatus for manufacturing customized cosmetics according to an exemplary embodiment of the present disclosure.

FIG. 1 is a diagram schematically illustrating an apparatus for manufacturing customized cosmetics according to an exemplary embodiment of the present disclosure. Referring to FIG. 1, an apparatus for manufacturing customized cosmetics according to an exemplary embodiment of the present disclosure may selectively include a skin measuring unit 110, an input unit 120, a control unit 130, a manufacturing unit 140, a memory unit 150, and a supplying unit 160.

The skin measuring unit 110 may measure skin divided based on a face region of a user, and generate a dosage form reference component skin measurement value.

The input unit 120 may input external signals, such as the dosage form reference component skin measurement value divided based on the face region of the user, an auxiliary dosage form reference component measurement value separately divided from the dosage form reference component skin measurement value, and a customized cosmetic kind selecting signal. The input unit 120 may be provided at one side of the apparatus for manufacturing customized cosmetics in the form of a keypad or a touch panel. The input unit 120 may be connected with the apparatus for manufacturing customized cosmetics in a wired or wireless form so that corresponding data may be input.

The control unit 130 performs operations, processing, and the like by a processor of an information processing device, and means a logical part of a program performing a specific function in a computer, and may be implemented with software, hardware, and the like. For example, the information processing device may be a personal computer, a handheld computer, a personal digital assistant (PDA), a mobile phone, a smart device, and a tablet device. The control unit 130 performs a series of control operations related to the manufacturing of customized cosmetics. Further, the control unit 130 may separately include the memory unit 150, which stores data related to the manufacturing of customized cosmetics.

The memory unit 150 is a device storing information, and may include various kinds of memory such as a non-volatile memory including a high-speed random access memory, a magnetic disk storage device, a flash memory device, and other non-volatile solid-state memory devices. In the memory unit 150, a dosage form reference component skin reference value corresponding to a dosage form reference component skin measurement value for a skin characteristic divided based on the face region of the user measured through the skin measuring unit 110 is stored. Herein, the dosage form reference component skin measurement value may be input through the input unit 120 and be stored in the memory unit 150. The memory unit 150 may serve to store an auxiliary dosage form reference component measurement value for external environment information input through the input unit 120, an auxiliary dosage form reference component reference value corresponding to the auxiliary dosage form reference component measurement value, and the like. Further, the memory unit 150 may also store data for a cosmetic dosage form reference component suitable for data for an individual skin characteristic of a user or each skin state, data, or a relevant program related to the manufacturing of customized cosmetics, and the like. The control unit 130 connected with the memory unit 150 may analyze the dosage form reference component skin measurement value, the auxiliary dosage form reference component measurement value, and the like of the user input through the skin measuring unit 110 and the input unit 120 when the customized cosmetics are manufactured according to the exemplary embodiment of the present disclosure, and automatically control the driving of the manufacturing unit 140 so as to manufacture a final dosage form component by appropriately combining a dosage form reference component and an auxiliary dosage form reference component appropriate for the analyzed measurement values to manufacture the customized cosmetics. The control unit 130 compares the dosage form reference component skin measurement value measured according to a predetermined programming and the dosage form reference component reference value stored in the memory unit 150, and determines a final dosage form component. Further, the control unit 130 performs a series of control operations for manufacturing customized cosmetics with the determined final dosage form component.

For example, when the dosage form reference component skin measurement value is input, the control unit 130 compares the dosage form reference component skin measurement value with the dosage form reference component skin reference value, and calculates a dosage form reference component skin measurement point. Then, the control unit 130 compares the auxiliary dosage form reference component measurement value with the auxiliary dosage form reference component reference value, and calculates an auxiliary dosage form reference component measurement point. Then, the control unit 130 determines a dosage form reference component based on the dosage form reference component skin measurement point, determines an auxiliary dosage form reference component based on the auxiliary dosage form reference component measurement point, and determines a final dosage form component by combining the dosage form reference component and the auxiliary dosage form reference component. Herein, when the kind of customized cosmetics is selected in the state where the dosage form reference component skin measurement value and the auxiliary dosage form reference component measurement value are input, the control unit 130 may determine a final dosage form component corresponding to the selected kind of customized cosmetics. Further, the control unit 130 may control so that the final dosage form component is injected to a cosmetic container by a predetermined capacity to manufacture the customized cosmetics. For example, the control unit 130 may output a manufacturing signal related to the manufacturing of the customized cosmetics so as to manufacture the customized cosmetics corresponding to the final dosage form component.

The manufacturing unit 140 is driven by receiving an input of the manufacturing signal related to the manufacturing of the customized cosmetics so as to manufacture the customized cosmetics corresponding to the final dosage form component analyzed by the control unit 130. In addition, after the control unit 130 determines the final dosage form component, the manufacturing unit 140 may also independently generate a manufacturing signal based on the determined final dosage form component. The manufacturing unit 140 manufactures the customized cosmetics with the final dosage form component corresponding to the dosage form reference component skin measurement value, the auxiliary dosage form reference component measurement value, and the selected kind of customized cosmetics. The manufacturing unit 140 may include a storing unit storing each of a dosage form reference component and an auxiliary dosage form reference component for manufacturing customized cosmetics. Herein, in the storing unit, a dosage form reference component storing unit of an individual capacity may be divided and formed. The dosage form reference component storing unit includes a moisture component storing unit, a winkle component storing unit, a skin elasticity component storing unit, and a sebum care component storing unit according to the exemplary embodiment of the present disclosure. Further, as necessary, the dosage form reference component storing unit may further include an auxiliary component storing unit storing each of a perfume component, a vitamin component, and an oil component.

The supplying unit 160 serves to supply the user with the customized cosmetics manufactured by the manufacturing unit 140. The supplying unit 160 may be implemented so as to automatically supply the customized cosmetics at every predetermined supply cycle based on a user in association with an existing unmanned delivery system. Further, the supplying unit 160 may be automatically implemented by utilizing a delivery robot or a drone for delivery.

In the meantime, the type of skin of the user may be generally divided into oily skin, dry skin, and complex skin. However, about 45% among the types of skin of the user is analyzed as complex skin and a skin state is different based on a face region, so that it may be difficult to manage the entire face with one specified component. 45% among the types of skin of the user corresponds to the complex skin and a skin characteristic may be different based on a face region by a complex mechanism of skin physiology. Because of this, there is a demand for customized cosmetics manufactured based on a skin measurement value measured based on a face region.

Figure 2:
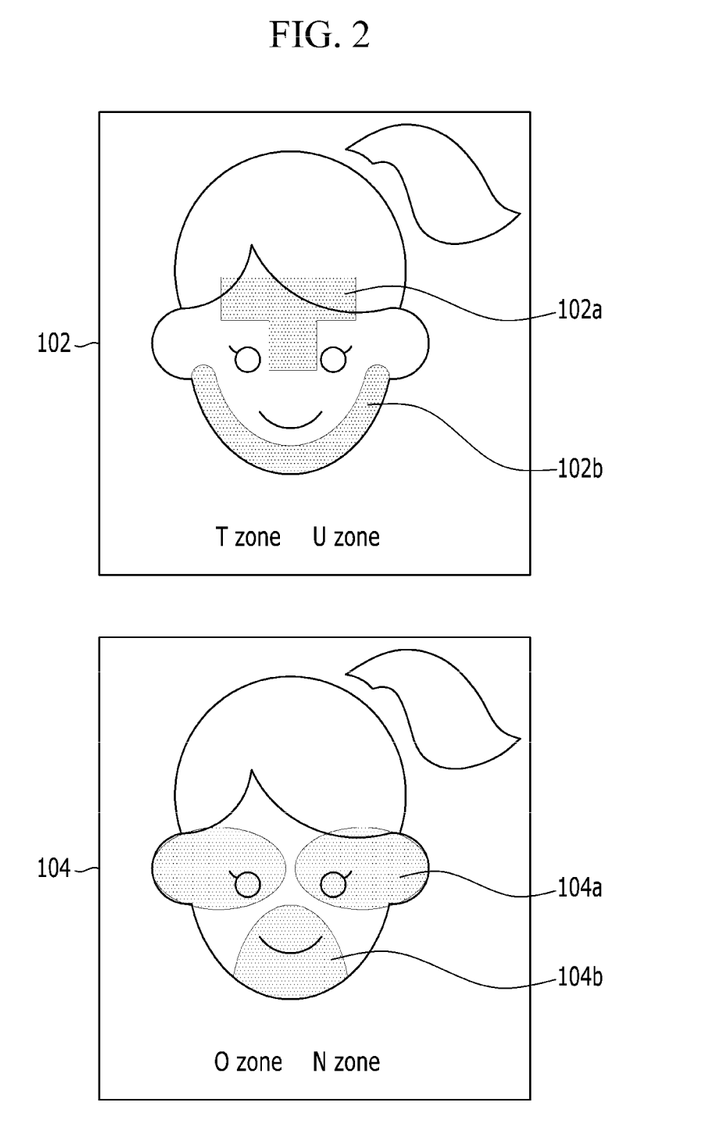
FIG. 2 is a diagram in which a face region of a user is divided into a first region that is an external region and a second region that is an internal region according to the exemplary embodiment of the present disclosure.

FIG. 2 is a diagram in which a face region of a user is divided into a first region 102 that is an external region and a second region 104 that is an internal region according to the exemplary embodiment of the present disclosure. Referring to FIG. 2, the face region of the user may include the first region 102 that is an external region and the second region 104 that is an internal region. Herein, the first region 102 may include a T zone covering a forehead line and a nose line, which are upper portions in an external region of the face region, and a U zone covering both lateral surface lines and a chin line, which are lower portions in the external region of the face region. Further, the second region 104 may include an O zone covering both eye surrounding lines and cheek lines in the internal region of the face region, and an N zone covering a noise periphery line and a mouth periphery line in the internal region of the face region. The T zone and the U zone of the first region 102 and the O zone and the N zone of the second region 104 are divided based on the region in consideration of a similar skin quality and a user intensive management region, and may also be divided based on another reference as necessary. As described above, the face region of the user is divided into the first region 102 that is the external region and the second region 104 that is the internal region, so that when customized cosmetics are manufactured, it is possible to appropriately adjust a dosage form reference component and a content of the dosage form reference component according to a skin state divided based on the face region of the user. Further, the user may use the customized cosmetics manufactured to be more suitable for the skin of the user, so that a side effect, such as skin problems, may not be generated or may be decreased.

Figure 3:
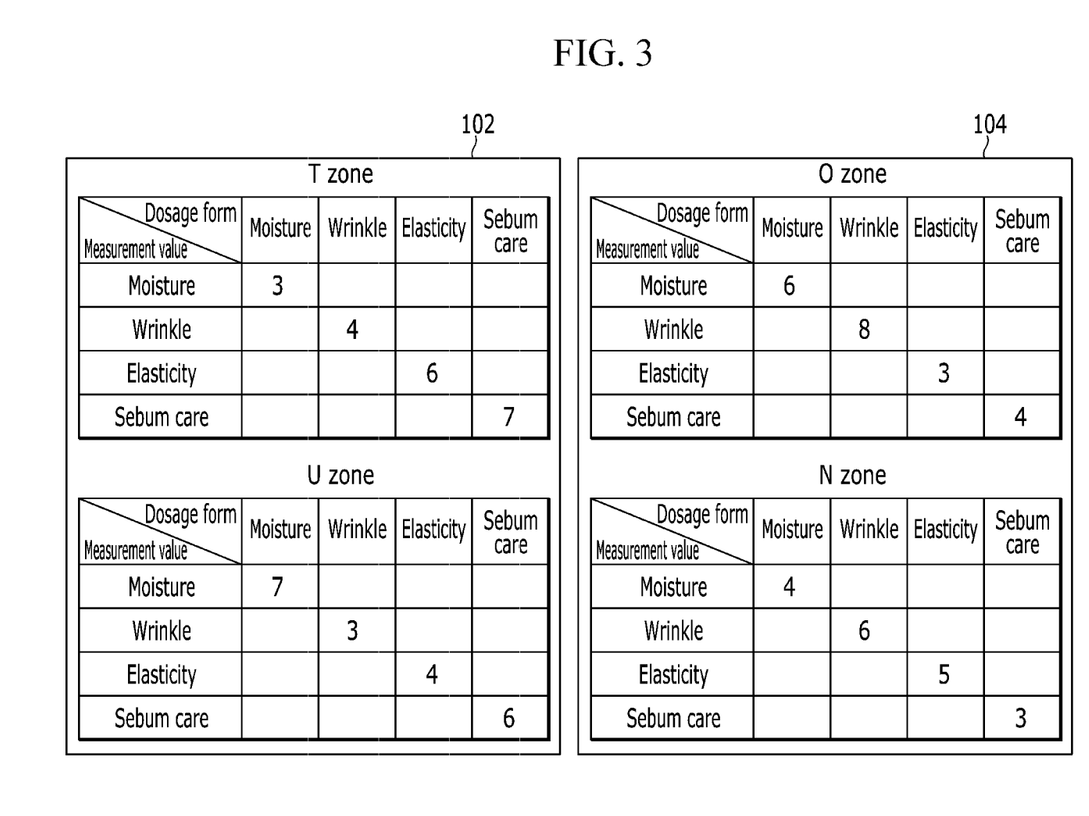
FIG. 3 is a diagram illustrating dosage form reference components and dosage form reference component skin measurement points for the first region and the second region according to the exemplary embodiment of the present disclosure.

FIG. 3 is a diagram illustrating dosage form reference components and dosage form reference component skin measurement points for the first region and the second region according to the exemplary embodiment of the present disclosure. Herein, the dosage form reference component may include components according to skin characteristics based on several regions based on a face of a user. For example, the dosage form reference component may include a moisture component for improving moisture, a wrinkle component for improving wrinkles, an elasticity component for maintaining skin elasticity, and a sebum care component for providing sebum care. Herein, the wrinkle improving component may include a component for managing thick wrinkles and fine wrinkles, and the elasticity component may include a component for delaying the degradation of skin elasticity. Further, the sebum care component may include a component for managing pores of the skin and helping a skin state to be maintained in a softer state. Further, the dosage form reference component skin measurement value includes a moisture component skin measurement value, a wrinkle component skin measurement value, an elasticity component skin measurement value, and a sebum care component skin measurement value. Further, the dosage form reference component skin measurement value may be compared with the dosage form reference component skin reference value, based on which the dosage form reference component including the basic component of customized cosmetics is selected, and may be calculated as a dosage form reference component skin measurement point.

Referring to FIG. 3, the dosage form reference component skin measurement value corresponding to each dosage form reference component is compared with the dosage form reference component skin reference value pre-stored in the memory unit 150, and is calculated as a dosage form reference component skin measurement point. The dosage form reference component skin measurement point may be calculated in a distribution of one point to eight points based on each dosage form reference component. That is, the dosage form reference component skin measurement value is compared with the predetermined dosage form reference component skin reference value, and the dosage form reference component skin reference value may be divided into a plurality of ranges so that the dosage form reference component skin measurement value is included. Further, the dosage form reference component skin reference value may be divided into appropriate stages based on each range, and calculated as a dosage form reference component skin measurement point. Accordingly, the dosage form reference component skin measurement value may be calculated as the dosage form reference component skin measurement point divided into one point to eight points according to the range, in which the dosage form reference component skin measurement value is included, among the plurality of divided ranges of the dosage form reference component skin reference value. For example, the moisture component skin measurement value may be measured by the value obtained by measuring a moisture ratio based on each face region, and the moisture component skin reference value may be pre-set with the eight stage ranges according to a moisture ratio.

More particularly, for example, the moisture component skin reference value may be divided into the first stage (1 to 10%), the second stage (11 to 20%), the third stage (21 to 30%), the fourth stage (31 to 50%), the fifth stage (51 to 70%), the sixth stage (71 to 80%), the seventh stage (81 to 90%), and the eighth stage (91 to 100%). Further, when the moisture component skin measurement value corresponds to the first stage of the moisture component skin reference value, the moisture component skin measurement point may be calculated as one point, and when the moisture component skin measurement value corresponds to the eighth stage of the moisture component skin reference value, the moisture component skin measurement point may be calculated as eight points. Referring to FIG. 3 in consideration of the contents, the moisture component skin measurement point among the dosage form reference component skin measurement points measured in the T zone may be calculated as three points, and the sebum care component skin measurement point may be calculated as seven points. Herein, the dosage form reference component skin measurement point may also be calculated by a percentage. For example, the dosage form reference component skin measurement point measured in the T zone may be calculated as the moisture component skin measurement point of 40% and the sebum care component skin measurement point of 80%. Further, in a priority of the dosage form reference component skin measurement point, which is the basis of the determination of the dosage form reference component, the moisture component skin measurement point may be set to the first rank, the wrinkle component skin measurement point may be set to the second rank, the elasticity component skin measurement point may be set to the third rank, and the sebum care component skin measurement point may be set to the fourth rank. The dosage form reference component skin measurement point and the priority may be reflected to the manufacturing of the final dosage form reference component of customized cosmetics.

In addition, a skin expert may diagnose or measure the skin of the user through the skin measuring unit 110. The user may particularly check a region including skin problems in his/her face region and the kind of skin problems through the skin measurement, in which the face region is sub-divided into the first region 102 and the second region 104. Further, the user may regularly measure the skin of his/her face region, so that the user may more precisely check a skin state of the face region in response to his/her body change or an external environment change. Accordingly, the user may have reliable skin measurement of the face region.

In the meantime, the skin measurement in the face region of the user may be different according to sebum and a moisture ratio of a skin surface state, sensitivity to external stimuli, wrinkles, a skin color, and an aging state of elasticity. Further, in the skin measurement, an external environment, such as ultraviolet rays, smoking, and stress, needs to be considered as well as an age and a genetic internal environment. Accordingly, it is necessary to manufacture cosmetics appropriate for skin of a user and a surrounding environment of the user in order to maintain healthier skin in consideration of the external environment of the exposure to ultraviolet rays and stress, as well as the skin of the user, when customized cosmetics are manufactured.

Figure 4:
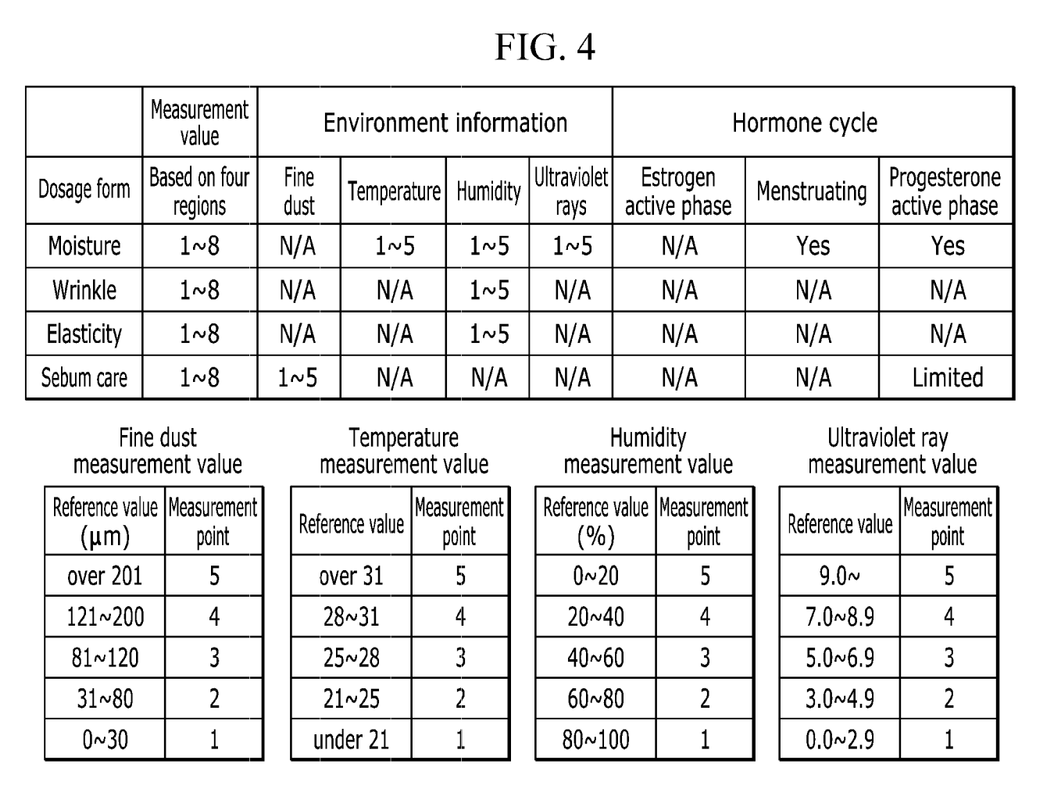
FIG. 4 is a diagram illustrating an example of auxiliary dosage form reference component reference values and auxiliary dosage form reference component measurement points for the auxiliary dosage form reference component measurement values according to the exemplary embodiment of the present disclosure.

FIG. 4 is a diagram illustrating an example of auxiliary dosage form reference component reference values and auxiliary dosage form reference component measurement points for the auxiliary dosage form reference component measurement values according to the exemplary embodiment of the present disclosure. Referring to FIG. 4, the dosage form reference component may include a moisture component, a wrinkle component, an elasticity component, and a sebum care component, and an auxiliary dosage form reference component measurement value may include a fine dust measurement value, a temperature measurement value, a humidity measurement value, an ultraviolet ray measurement value, and a menstrual cycle measurement value. The dosage form reference component may include a whitening component, apart from the elasticity component. Accordingly, the dosage form reference component may include a moisture component, a wrinkle component, a whitening component, and a sebum care component, as necessary. As illustrated in FIG. 4, the exemplary embodiment of the present disclosure includes an auxiliary dosage form reference component measurement value considering a separate external environment, in addition to the dosage form reference component skin measurement value measured based on each face region of the user. The auxiliary dosage form reference component measurement value is compared with a predetermined auxiliary dosage form reference component reference value, and the auxiliary dosage form reference component reference value may be divided into a plurality of ranges so that the auxiliary dosage form reference component measurement value is included. Further, the auxiliary dosage form reference component reference value may be divided into appropriate stages based on each range, and calculated as an auxiliary dosage form reference component measurement point. Accordingly, the auxiliary dosage form reference component measurement value may be calculated as the dosage form reference component measurement point divided into one point to five points according to the range, in which the auxiliary dosage form reference component measurement value is included, among the plurality of divided ranges of the auxiliary dosage form reference component reference value. The auxiliary dosage form reference component measurement value may include a predetermined weather change measurement value corresponding to environment information and a hormone cycle measurement value. The weather change measurement value may include a fine dust measurement value, a temperature measurement value, a humidity measurement value, and an ultraviolet ray measurement value with respect to a nation, a region, and a month-specific weather change. The weather change measurement value may be updated by a big data value with respect to an annual weather change and be applied. For example, the weather change measurement value may be updated by applying a predetermined weight value to data of the previous three years. Further, the hormone cycle measurement value may include a menstrual cycle measurement value.

More particularly, referring to FIG. 4, for example, a fine dust reference value may be divided into the first stage (0 to 30 μm), the second stage (31 to 80 μm), the third stage (81 to 120 μm), the fourth stage (121 to 200 μm), and the fifth stage (from 121 μm). Further, when the fine dust measurement value is measured as 23 μm and corresponds to the first stage of the fine dust reference value, the fine dust measurement point may be calculated as one point, and when the fine dust measurement value is measured as 123 μm and corresponds to the fifth stage of the fine dust reference value, the fine dust measurement point may be calculated as five points.

The temperature reference value may be divided into the first stage (20° C. or lower), the second stage (21 to 24° C.), the third stage (25 to 27° C.), the fourth stage (28 to 30° C.), and the fifth stage (31° C. or higher). Further, when the temperature measurement value is measured as 23° C. and corresponds to the second stage of the temperature reference value, the temperature measurement point may be calculated as two points, and when the temperature measurement value is measured as 34° C. and corresponds to the fifth stage of the temperature reference value, the temperature measurement point may be calculated as five points.

The humidity reference value may be divided into the first stage (81 to 100%), the second stage (61 to 80%), the third stage (41 to 60%), the fourth stage (21 to 40%), and the fifth stage (0 to 20%). Further, when the humidity measurement value is measured as 90% and corresponds to the first stage of the humidity reference value, the humidity measurement point may be calculated as one point, and when the humidity measurement value is measured as 10% and corresponds to the fifth stage of the humidity reference value, the humidity measurement point may be calculated as five points.

The ultraviolet ray reference value may be divided into the first stage (0.0 to 2.9), the second stage (3.0 to 4.9), the third stage (5.0 to 6.9), the fourth stage (7.0 to 8.9), and the fifth stage (9.0 or more). Further, when the ultraviolet ray measurement value is measured as 2 and corresponds to the first stage of the ultraviolet ray reference value, the ultraviolet ray measurement point may be calculated as one point, and when the ultraviolet ray measurement value is measured as 9.5 and corresponds to the fifth stage of the ultraviolet ray reference value, the ultraviolet ray measurement point may be calculated as five points. Herein, the ultraviolet ray measurement value may be measured so that an output voltage is generated by as much as the amount of ultraviolet rays received. Further, the ultraviolet ray reference value may be simply displayed by dividing an output voltage measured by an ultraviolet ray measuring device into five stages. For example, 0.0 to 2.9 that is the range of the first stage of the ultraviolet ray reference value is the simple display of an output voltage of 0 mV to 299 mV. The range or a measurable intensity of the ultraviolet rays measurable by using the ultraviolet ray measuring device may be differently adjusted according to the kind of ultraviolet ray measuring device.

In the meantime, the auxiliary dosage form reference component refers to a component for selecting the amount added to or subtracted from the existing dosage form reference component determined for the dosage form reference component skin measurement value according to the auxiliary dosage form reference component measurement value, not a separate additional component. That is, the amount of the corresponding dosage form reference component may be added to be increased or decreased according to the auxiliary dosage form reference component measurement value. Accordingly, the auxiliary dosage form reference component may be formed of the same component as the dosage form reference component.

The fine dust measurement point may be reflected when the sebum care component skin measurement point is selected as the dosage form component skin measurement point. For example, the fine dust measurement point may be divided into one point to five points. Further, when the fine dust measurement points are one point and two points, it may be set such that a separate point is not added. When the fine dust measurement point is three points or more, a final fine dust measurement point may be calculated with a final value obtained by multiplying the existing sebum care component skin measurement point by an added point for the fine dust measurement point. Herein, the added point for the fine dust measurement point may be set to a value of the existing fine dust measurement point×0.5. Further, a final sebum care component skin measurement point may be set by pre-setting a reference value corresponding to a time at which a large amount of fine dust is generated. Herein, the time at which a large amount of fine dust is generated may be set based on backup data prior to the current year, and the reference value may also be set based on backup data. For example, the time at which a large amount of fine dust is generated may be set to March and April. Further, the reference value for the fine dust may be set to three points.

In the meantime, the temperature measurement point may be reflected when the moisture component skin measurement point is selected as the dosage form reference component skin measurement point. For example, the temperature measurement point may be divided into one point to five points. Further, when the temperature measurement points are one point and two points, it may be set such that there is no separate added point. When the temperature measurement point is three points or more, a final moisture component measurement point may be calculated with a final value obtained by multiplying the existing moisture component skin measurement point by an added point for the temperature measurement point. Herein, the added point for the temperature measurement point may be set to a value of the existing temperature measurement point×0.5. Further, a final moisture component skin measurement point may be set by pre-setting a reference value corresponding to a time at which the generation of a high temperature is expected. Herein, the time at which the generation of the high temperature is expected may be set based on backup data prior to the current year, and the reference value may also be set based on backup data. For example, the time at which the generation of the high temperature is expected may be set to June, July, August, and September. Further, the reference value for the high temperature may be set to three points.

In the meantime, the humidity measurement point may be reflected when the moisture component skin measurement point, the wrinkle component skin measurement point, and the elasticity component skin measurement point are selected as the dosage form reference component skin measurement point. For example, the humidity measurement point may be divided into one point to five points. Further, when the humidity measurement points are one point (81 to 100%) and two points (61 to 80%), it may be set such that a separate point is not added and subtracted for the wrinkle component skin measurement point and the elasticity component skin measurement point. In the meantime, in the case of the moisture component skin measurement point, it may be set such that a separate point is added and subtracted. For example, when the humidity measurement point is one point or two points, a final moisture component skin measurement point may be set with a final value obtained by multiplying the moisture component skin measurement point by an added/subtracted point for the humidity measurement point. Herein, the added/subtracted point for the humidity measurement point may be set to a value of the existing humidity measurement point×0.5. In this case, even though the added/subtracted point for the humidity measurement point is smaller than the third humidity measurement point, it may be set such that the added/subtracted point for the humidity measurement point is not changed. When the humidity measurement points are three points (0 to 60%) or more, a final dosage form component skin measurement point may be set with a final value obtained by multiplying each of the existing moisture component skin measurement point, the wrinkle component skin measurement point, and the elasticity component skin measurement point by the added/subtracted point for the humidity measurement point. Herein, the added/subtracted point for the humidity measurement point may be set to a value of the existing humidity measurement point×0.5.

In the meantime, the ultraviolet ray measurement point may be reflected when the moisture component skin measurement point is selected as the dosage form reference component skin measurement point. For example, the ultraviolet ray measurement point may be divided into one point to five points. Further, when the ultraviolet ray measurement points are one point and two points, it may be set such that there is no separate added point for the moisture component skin measurement point. When the ultraviolet ray measurement points are three points or more, a final moisture component skin measurement point may be set with a final value obtained by multiplying the existing moisture component skin measurement point by an added point for the ultraviolet ray measurement point. Herein, the added point for the ultraviolet ray measurement point may be set to a value of the existing ultraviolet ray measurement point×0.5. In the meantime, when the ultraviolet ray measurement points are four points or more, it may also be set such that a separate additive component is recommended for blocking ultraviolet rays.

In the meantime, the menstrual cycle measurement point may be selectively reflected to the dosage form reference component skin measurement point only when a user is a women. For example, the menstrual cycle measurement point may be divided into an estrogen active phase, a menstruation phase, and a progesterone active phase. Further, when the menstrual cycle measurement value is the estrogen active phase, it may be set such that there is no separate added point for the dosage form reference component skin measurement point. When the menstrual cycle measurement points are the menstruation phase and the progesterone active phase, a moisture component content may be the largest regardless of the moisture component skin measurement point. Further, the final sebum care component skin measurement point may be set so that the sebum care component measurement point is not reflected regardless of the point ranking in the progesterone active phase. Accordingly, a service which delivers customized cosmetics to a user at every predetermined period in consideration of a menstrual cycle of the user is available.

In the meantime, the auxiliary dosage form reference component may also further include a nutritive component, an incense component, and the like in addition to the whitening component. Herein, the whitening component may include a component which solves pigmentation such as freckles, a mole, and a dark spot of a face, and generally makes an irregular skin color be brighter and more uniform. That is, in the exemplary embodiment of the present disclosure, it is possible to manufacture and sell new customized cosmetics by a scheme of adding or mixing pigments, a nutritive component, perfume, and the like to customized cosmetics as necessary.

As described above, according to the exemplary embodiment of the present disclosure, it is possible to provide a user with more appropriate customized cosmetics based on a dosage form reference component skin measurement value measured based on each face region of the user and an auxiliary dosage form reference component measurement value input according to external environment information. That is, when customized cosmetics are manufactured, a dosage form reference component and a content of the dosage form reference component, and an auxiliary dosage form reference component added to the dosage form reference component and a content of the auxiliary dosage form reference component, may be appropriately adjusted according to a skin state of a user and an external environment. Because of this, a user may receive and use customized cosmetics which are manufactured in accordance with user's skin and external environment information at an appropriate time. Accordingly, a user may receive and use a fresher product at a product required time so that a side effect such as skin problems may not be generated or may be minimized. Further, a user may also receive various information including skin measurement information and external environment information, based on which the user is capable of selecting appropriate cosmetics. Accordingly, it is possible to further improve reliability of customized cosmetics by selecting while reflecting an auxiliary dosage form reference component measurement value including external environment information, in addition to the dosage form reference component skin measurement value. Further, it is possible to provide an appropriate guide function for a lifestyle and skin management of a user.

Figure 5:
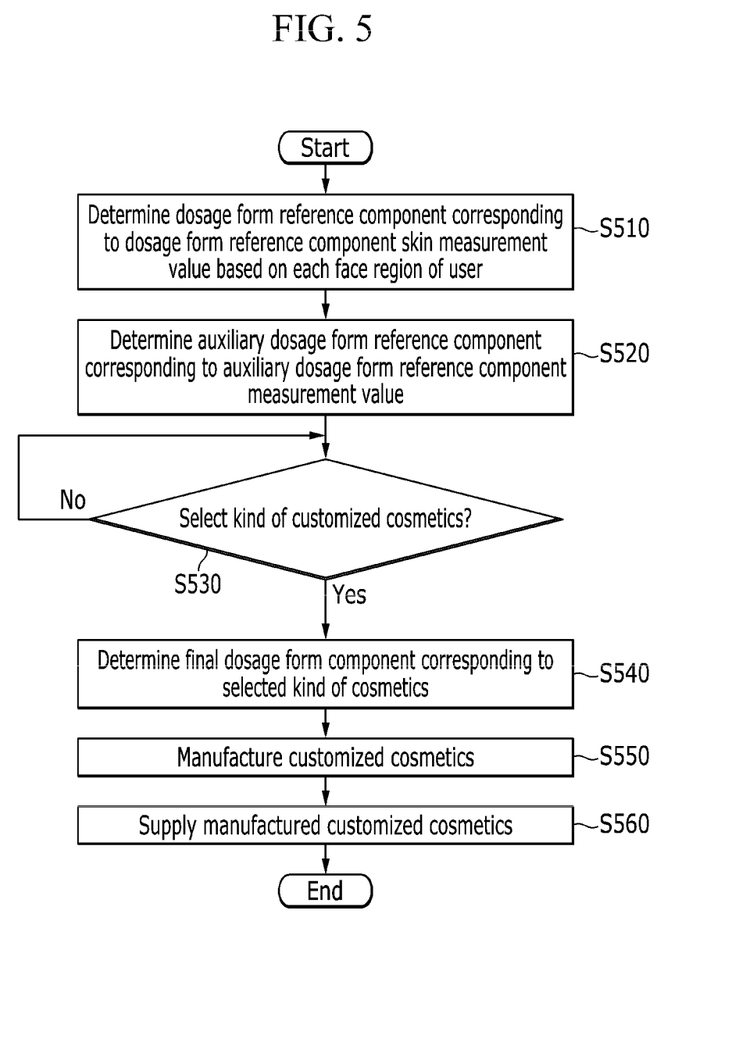
FIG. 5 is a flowchart illustrating a method of manufacturing customized cosmetics according to an exemplary embodiment of the present disclosure.

FIG. 5 is a flowchart illustrating a method of manufacturing customized cosmetics according to an exemplary embodiment of the present disclosure. The method of manufacturing customized cosmetics according to the exemplary embodiment of the present disclosure will be described with reference to FIGS. 1 to 5.

Referring to FIG. 5, the control unit 130 checks an input of a dosage form reference component skin measurement value based on each face region of a user (S510). Herein, the dosage form reference component skin measurement value may be measured by the skin measuring unit 110 and input, and may also be input through the input unit 120. The dosage form reference component skin measurement value is stored in the memory unit 150. Next, the control unit 130 checks an input of an auxiliary dosage form reference component measurement value separately divided from the dosage form reference component skin measurement value (S520). The auxiliary dosage form reference component measurement value may be input through the input unit 120. The auxiliary dosage form reference component measurement value is stored in the memory unit 150. When the kind of customized cosmetics is selected in the state where the dosage form reference component skin measurement value and the auxiliary dosage form reference component measurement value are input (S530), the control unit 130 compares the input dosage form reference component skin measurement value with a dosage form reference component skin reference value stored in the memory unit 150, and calculates a dosage form reference component measurement point. Then, the control unit 130 compares the auxiliary dosage form reference component measurement value with an auxiliary dosage form reference component reference value stored in the memory unit 150, and calculates an auxiliary dosage form reference component measurement point. Then, the control unit 130 determines a dosage form reference component based on the dosage form reference component skin measurement point, determines an auxiliary dosage form reference component based on the auxiliary dosage form reference component measurement point, and determines a final dosage form component by combining the dosage form reference component and the auxiliary dosage form reference component. That is, the control unit 130 analyzes and determines a dosage form reference component based on the dosage form reference component measurement point corresponding to the dosage form reference component skin measurement value, analyzes and determines an auxiliary dosage form reference component which is an additional component based on the auxiliary dosage form reference component measurement point corresponding to the auxiliary dosage form reference component measurement value, and determines a final dosage form component by combining the determined dosage form reference component and auxiliary dosage form reference component (S540).

Next, the control unit 130 outputs a manufacturing signal related to the manufacturing of the customized cosmetics so as to manufacture the customized cosmetics corresponding to the analyzed final dosage form component. The control unit 130 outputs the manufacturing signal and provides the manufacturing unit 140 with the manufacturing signal to manufacture the customized cosmetics with the final dosage form component corresponding to the dosage form reference component skin measurement value, the auxiliary dosage form reference component measurement value, and the selected kind of customized cosmetics (S550), and performs a series of control operations for providing the user with the manufactured customized cosmetics (S560).

In the meantime, the kind of customized cosmetics selected in operation S530 may include a premium type and a standard type. For example, when the customized cosmetics of the premium type are selected in operation S530, the control unit 130 calculates a dosage form reference component-specific skin measurement point by a predetermined reference among the plurality of dosage form reference component skin measurement points calculated in the first region 102 and the second region 104 for each dosage form reference component. Then, the control unit 130 selects two high rank points including the first rank skin measurement point and the second rank skin measurement point among the dosage form reference component-specific skin measurement points, and sets a final dosage form component based on the first rank skin measurement point and the second rank skin measurement point. For example, the control unit 130 may set a final dosage form component with the first rank skin measurement point and the second rank skin measurement point, which are the higher dosage form reference component skin measurement points calculated based on each dosage form reference component for each region among the dosage form reference component skin measurement values measured in the first region 102 and the second region 104. Herein, in order to discriminate the first rank skin measurement point and the second rank skin measurement point for each dosage form reference component, the predetermined reference may be set with a maximum value among the dosage form reference component-specific skin measurement values.

For example, in FIG. 3, a maximum value of the moisture component skin measurement point is seven points, a maximum value of the wrinkle component skin measurement point is eight points, a maximum value of the elasticity component skin measurement point is six points, and a maximum value of the sebum care component skin measurement point is seven points. In this state, first, the first rank skin measurement points are eight points, which is the maximum value of the wrinkle component skin measurement point. Then, the second rank skin measurement points are seven points, which is the maximum value of the moisture component skin measurement point, and seven points, which is the maximum value of the sebum care component skin measurement point. However, the priority of the dosage form reference component skin measurement point may be set as the first rank moisture component skin measurement point, the second rank wrinkle component skin measurement point, the third rank elasticity component skin measurement point, and the fourth rank sebum care component skin measurement point, so that the final second rank skin measurement points are seven points, which is the maximum value of the moisture component skin measurement point having the higher priority.

Further, in order to discriminate the first rank skin measurement point and the second rank skin measurement point based on each dosage form reference component, the predetermined reference may be a maximum value among the average values of the dosage form reference component-specific skin measurement values or a maximum value in the sum of the dosage form reference component-specific skin measurement values. For example, in FIG. 3, an average value of the moisture component skin measurement points is 5 points, an average value of the wrinkle component skin measurement points is 5.25 points, an average value of the elasticity component skin measurement points is 4.5 points, and an average value of the sebum care component skin measurement points is 5 points. In this state, first, the first rank skin measurement points are 5.25 points, which is an average value of the wrinkle component skin measurement points. Then, the second rank skin measurement points are 5 points, which is an average value of the moisture component skin measurement points, and 5 points, which is an average value of the sebum care component skin measurement points. However, in consideration of the priority of the dosage form reference component skin measurement point, the final second rank skin measurement points are five points, which is the average value of the moisture component skin measurement points.

In the meantime, when the customized cosmetics of the standard type are selected in operation S530, the control unit 130 calculates a dosage form reference component-specific skin measurement point by a predetermined reference among the plurality of dosage form reference component skin measurement points calculated in the first region 102 for each dosage form reference component. Then, the control unit 130 selects two high rank points including the first rank skin measurement point and the second rank skin measurement point among the dosage form reference component-specific skin measurement points, and sets a final dosage form component based on the first rank skin measurement point and the second rank skin measurement point. For example, the control unit 130 may set a final dosage form component with the first rank skin measurement point and the second rank skin measurement point, which are the higher dosage form reference component-specific skin measurement points calculated based on the dosage form reference component skin measurement value measured in the first region 102. Herein, in order to discriminate the first rank skin measurement point and the second rank skin measurement point based on each dosage form reference component, the predetermined reference may be a maximum value among the average values of the dosage form reference component-specific skin measurement values or a maximum value in the sum of the dosage form reference component-specific skin measurement values.

In the meantime, when the customized cosmetics of the premium type are selected in operation S530, the control unit 130 may also set an added point to be applied to the dosage form reference component skin measurement value measured in the second region 104. The added point is applied to the dosage form reference component skin measurement value measured in the second region 104, so that it is possible to more certainly manage the second region 104, which may be divided as the more sensitive and important face region than the first region 102, and increase skin improvement efficiency.

Figure 6:
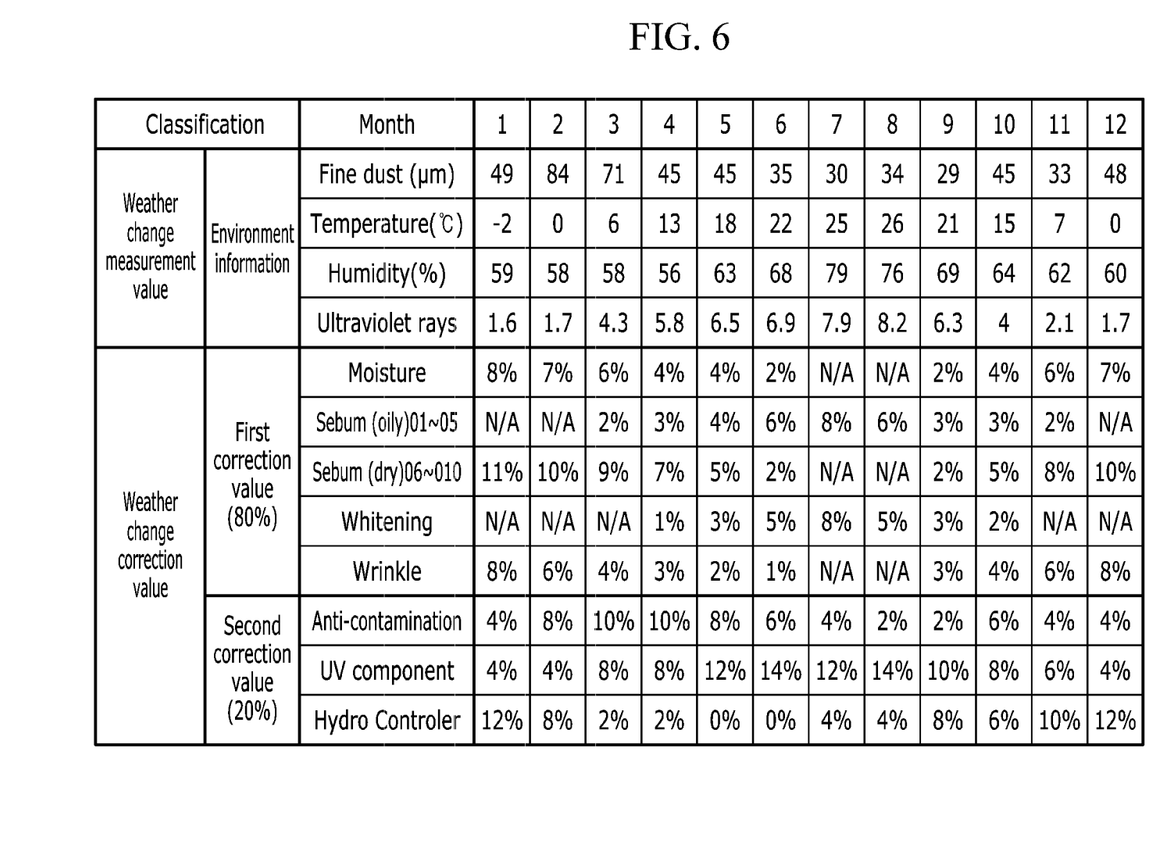
FIG. 6 is a diagram illustrating an example of weather change correction values for weather change measurement values according to an exemplary embodiment of the present disclosure.

FIG. 6 is a diagram illustrating an example of weather change correction values for weather change measurement values according to an exemplary embodiment of the present disclosure. Referring to FIGS. 5 and 6, the control unit 130 may set a weather change correction value, which is an added point, to be applied to the dosage form reference component skin measurement value measured in the second region 104. Herein, the dosage form reference component skin measurement value may include the moisture component skin measurement value, the wrinkle component skin measurement value, the whitening component skin measurement value, and the sebum care component skin measurement value. Further, the weather change correction value may be set according to a monthly weather change measurement value as illustrated in FIG. 6. The weather change correction value may include a first correction value including a moisture component correction value, a sebum component correction value, a whitening component correction value, and a wrinkle component correction value, and a second correction value including an anti-contamination component correction value, an ultraviolet component correction value, and a hydro controller component correction value. The first correction value may be set with a range within 80 wt % of the total correction value, and the second correction value may be set with a range within 20 wt % of the total correction value. The second correction value may be calculated as a remaining value based on 100 wt % after the first correction value is applied, and be applied.

The control unit 130 may select two high rank points including the first rank skin measurement point and the second rank skin measurement point among the plurality of dosage form reference component skin measurement points calculated in the first region and the second region based on each dosage form reference component. The control unit 130 sets a final dosage form component based on a final first rank skin measurement point and a second rank skin measurement point calculated by adding the predetermined weather change correction value to each of the first rank skin measurement point and the second rank skin measurement point point. Herein, the weather change correction value may also be designed so as to be added only to the first rank skin measurement point according to the program setting of the control unit 130.

Further, the control unit 130 may also set a final dosage form component based on a final first rank skin measurement point and a second rank skin measurement point calculated by adding a predetermined face region correction value to each of the first rank skin measurement point and the second rank skin measurement point. For example, in the case of the wrinkle component measurement value measured in the O zone around the eyes, which are easily wrinkled, the control unit 130 may set a final dosage form component based on the final first rank skin measurement point and second rank skin measurement point calculated by adding the predetermined face region correction value. By the method, in the case of the moisture component measurement value measured in the T zone around the forehead, which has a lot of oil, the control unit 130 may set a final dosage form component based on the final first rank skin measurement point and second rank skin measurement point calculated by adding the predetermined face region correction value. Herein, the face region correction value may also be designed so as to be added only to the first rank skin measurement point according to the program setting of the control unit 130.

The customized cosmetics manufactured according to the exemplary embodiment of the present disclosure may be manufactured with the final dosage form component appropriate for the weather change and an individual skin state based on the skin measurement data for each face region of the user measured by the separate skin measuring unit 110 and the weather change correction value. That is, in the exemplary embodiment of the present disclosure, a face region is divided so that an individual skin characteristic is more accurately measured and is managed in the face region of a user, and a dosage form reference component skin measurement value corresponding to each divided face region is measured. Further, a dosage form reference component corresponding to a specified face region is selected by applying a predetermined point and a weather change correction value to a dosage form reference component skin measurement value measured in a face region, and a final dosage form component is formed by appropriately combining an auxiliary dosage form reference component as necessary, thereby manufacturing customized cosmetics. Accordingly, a user may use customized cosmetics manufactured in consideration of an individual skin characteristic, rather than cosmetics that are mass-manufactured by a general cosmetic manufacturing company in consideration of taste or a skin characteristic of an average consumer. Further, it is also possible to manufacture more differentiated customized cosmetics by using a natural material itself or a cosmetic raw material in the form of the processed natural material according to the taste of a user. Accordingly, a user may easily select a cosmetic component appropriate for a weather change and his/her skin characteristics, and regularly receive and use cosmetics which are appropriate for his/her skin and are fresh.

While this disclosure has been described in connection with what is presently considered to be practical exemplary embodiments, it is to be understood that the disclosure is not limited to the disclosed embodiments. On the contrary, it is intended to cover various modifications and equivalent arrangements included within the spirit and scope of the appended claims.

The invention claimed is:

1. An apparatus for manufacturing customized cosmetics, the apparatus comprising:
   a memory unit, which stores a dosage form reference component skin measurement value divided based on each face region of a user, an auxiliary dosage form reference component measurement value considering a separate external environment, a dosage form reference component skin reference value corresponding to the dosage form reference component skin measurement value, and an auxiliary dosage form reference component reference value corresponding to the auxiliary dosage form reference component measurement value; and
   a control unit, which is operated by a processor of an information processing device, and compares the dosage form reference component skin measurement value with the dosage form reference component skin reference value and calculates a dosage form reference component skin measurement point, compares the auxiliary dosage form reference component measurement value with the auxiliary dosage form reference component reference value and calculates an auxiliary dosage form reference component measurement point, determines a determined dosage form reference component based on the dosage form reference component skin measurement point, determines a determined auxiliary dosage form reference component based on the auxiliary dosage form reference component measurement point, and determines a final dosage form component by combining the determined dosage form reference component and the determined auxiliary dosage form reference component.

2. A method of manufacturing customized cosmetics, the method comprising the steps of:
storing a dosage form reference component skin measurement value divided based on each face region of a user, and an auxiliary dosage form reference component measurement value considering a separate external environment; and
after the dosage form reference component skin measurement value and the auxiliary dosage form reference component measurement value are stored, reading a dosage form reference component skin reference value corresponding to the dosage form reference component skin measurement value and an auxiliary dosage form reference component reference value corresponding to the auxiliary dosage form reference component measurement value from a memory unit, and comparing the dosage form reference component skin measurement value with the dosage form reference component skin reference value and calculating a dosage form reference component skin measurement point, comparing the auxiliary dosage form reference component measurement value with the auxiliary dosage form reference component reference value and calculating an auxiliary dosage form reference component measurement point, determining a determined dosage form reference component based on the dosage form reference component skin measurement point, determining a determined auxiliary dosage form reference component based on the auxiliary dosage form reference component measurement point, and determining a final dosage form component by combining the determined dosage form reference component and the determined auxiliary dosage form reference component.

3. The method of claim 2, wherein the face region of the user includes a first region, which is an external region, and a second region, which is an internal region, the first region includes a T zone covering a forehead line and a nose line, which are upper portions in the external region of the face region, and a U zone covering both lateral lines and a chin line, which are lower portions in the external region of the face region, and the second region includes an O zone covering both eye surrounding lines and cheek lines in the internal region of the face region, and an N zone covering the nose surrounding line and a mouth surrounding line in the internal region of the face region.

4. The method of claim 2, wherein the dosage form reference component skin measurement value includes a moisture component skin measurement value, a wrinkle component skin measurement value, an elasticity component skin measurement value, and a sebum care component skin measurement value, and the auxiliary dosage form reference component measurement value includes one or more of a weather change measurement value including a fine dust measurement value, a temperature measurement value, a humidity measurement value, and an ultraviolet ray measurement value, and a menstrual cycle measurement value.

5. The method of claim 2, wherein the dosage form reference component skin measurement value includes a moisture component skin measurement value, a wrinkle component skin measurement value, a whitening component skin measurement value, and a sebum care component skin measurement value, and the auxiliary dosage form reference component measurement value includes one or more of a weather change measurement value including a fine dust measurement value, a temperature measurement value, a humidity measurement value, and an ultraviolet ray measurement value, and a menstrual cycle measurement value.

6. The method of claim 5, further comprising receiving an input of a selection signal for a kind of customized cosmetics, wherein the kind of customized cosmetics includes a premium type and a standard type, the face region of the user includes a first region, which is an external region, and a second region, which is an internal region, when the customized cosmetics of the premium type are manufactured, a dosage form reference component-specific skin measurement point is calculated by a predetermined reference among a plurality of dosage form reference component skin measurement points calculated in the first region and the second region based on each dosage form reference component, two high rank points including a first rank skin measurement point and a second rank skin measurement point are selected among the dosage form reference component-specific skin measurement point, and the final dosage form component is set based on the first rank skin measurement point and the second rank skin measurement point, and when the customized cosmetics of the standard type are manufactured, the dosage form reference component-specific skin measurement point is calculated by a predetermined reference among the plurality of dosage form reference component skin measurement points calculated in the first region, two high rank points including the first rank skin measurement point and the second rank skin measurement point are selected among the dosage form reference component-specific skin measurement point, and the final dosage form component is set based on the first rank skin measurement point and the second rank skin measurement point.

7. The method of claim 5, wherein the face region of the user includes a first region, which is an external region, and a second region, which is an internal region, and two high rank points including a first rank skin measurement point and a second rank skin measurement point are selected among a plurality of dosage form reference component skin measurement points calculated in the first region and the second region based on each dosage form reference component, and the final dosage form component is set based on a final first rank skin measurement point and the second rank skin measurement point calculated by adding a predetermined weather change correction value to each of the first rank skin measurement point and the second rank skin measurement point.

8. The method of claim 7, wherein the weather change correction value is set according to a time period-specific weather change measurement value, and the weather change correction value includes a first correction value including a moisture component correction value, a sebum component correction value, a whitening component correction value, and a wrinkle component correction value, and a second correction value including an anti-contamination component correction value, an ultraviolet component correction value, and a hydro controller component correction value.

* * * * *